(12) United States Patent
Lee et al.

(10) Patent No.: US 10,206,966 B2
(45) Date of Patent: *Feb. 19, 2019

(54) METHOD FOR INDUCING DOPAMINE PRODUCTION OF DOPAMINERGIC CELLS

(71) Applicant: Chen-Yu Lee, Taipei (TW)

(72) Inventors: Chen-Yu Lee, Taipei (TW); Kang-Wei Chang, Taoyuan County (TW); Chuang-Hsin Chiu, Taipei (TW); Yan-Chih Liao, Taipei (TW); Dueng-Yuan Hueng, Taipei (TW); Yuan-Hao Chen, Taipei (TW)

(73) Assignee: Chen-Yu Lee, Taipei (TW)

( * ) Notice: Subject to any disclaimer, the term of this patent is extended or adjusted under 35 U.S.C. 154(b) by 772 days.

This patent is subject to a terminal disclaimer.

(21) Appl. No.: 14/534,556

(22) Filed: Nov. 6, 2014

(65) Prior Publication Data

US 2016/0129069 A1    May 12, 2016

(51) Int. Cl.
| | | |
|---|---|---|
| *A61K 36/9068* | (2006.01) | |
| *A61K 36/258* | (2006.01) | |
| *A61K 36/484* | (2006.01) | |
| *A61K 36/539* | (2006.01) | |
| *A61K 36/54* | (2006.01) | |

(52) U.S. Cl.
CPC ........ *A61K 36/9068* (2013.01); *A61K 36/258* (2013.01); *A61K 36/484* (2013.01); *A61K 36/539* (2013.01); *A61K 36/54* (2013.01); *A61K 2236/00* (2013.01)

(58) Field of Classification Search
CPC .............. A61K 2300/00; A61K 36/484; A61K 36/9068; A61K 36/539; A61K 36/54; A61K 36/258

See application file for complete search history.

(56) References Cited

U.S. PATENT DOCUMENTS

| | | | | |
|---|---|---|---|---|
| 8,003,140 B1 * | 8/2011 | Lee | ...................... | A61K 36/076 424/725 |
| 8,277,851 B2 * | 10/2012 | Lee | ........................ | A61K 35/32 424/725 |

OTHER PUBLICATIONS

Clarke, Zoe "Epidepride" xPharm: The Comprehensive Pharmacology Reference (Elsevier Inc.), 2007, pp. 1-3. .doi:10.1016/B978-008055232-3.61694-0.*
Zhao,Q. et al "A specialized flavone biosynthetic pathway has evolved in the medicinal plant, Scutellaria baicalensis", Sci Adv Apr. 8, 2016, 2(4), pp. 1-15 (e1501780; doi: 10.1126/sciadv. 1501780).*
Ittiyavirah SP, et al, Biomedicine & Aging Pathology, Oct. 1, 2014,4,pp. 369-376. (Year: 2014).*
Blaylock R, Newsmax, Feb. 1, 2017, retrieved from <URL:newsmax. com/PrintTemplate.aspx/?nodeid=771551>, 2 pages. (Year: 2017).*
Li X-Z, et al, Fitoterapia 84 (2013) 273-285. (Year: 2013).*

\* cited by examiner

*Primary Examiner* — Aaron J Kosar

(74) *Attorney, Agent, or Firm* — Bacon & Thomas, PLLC

(57) ABSTRACT

A method for inducing a proliferation of dopaminergic cells in a subject in need, comprising: administering a herbal medicinal composition to a subject in need, wherein the herbal medicinal composition comprises: *Ginseng* Radix, *Glycyrrhiza uralensis*, *Zingiber officinale* Roscoe, *Cinnamomum cassia* Presl., and Scutellariae Radix.

8 Claims, 1 Drawing Sheet

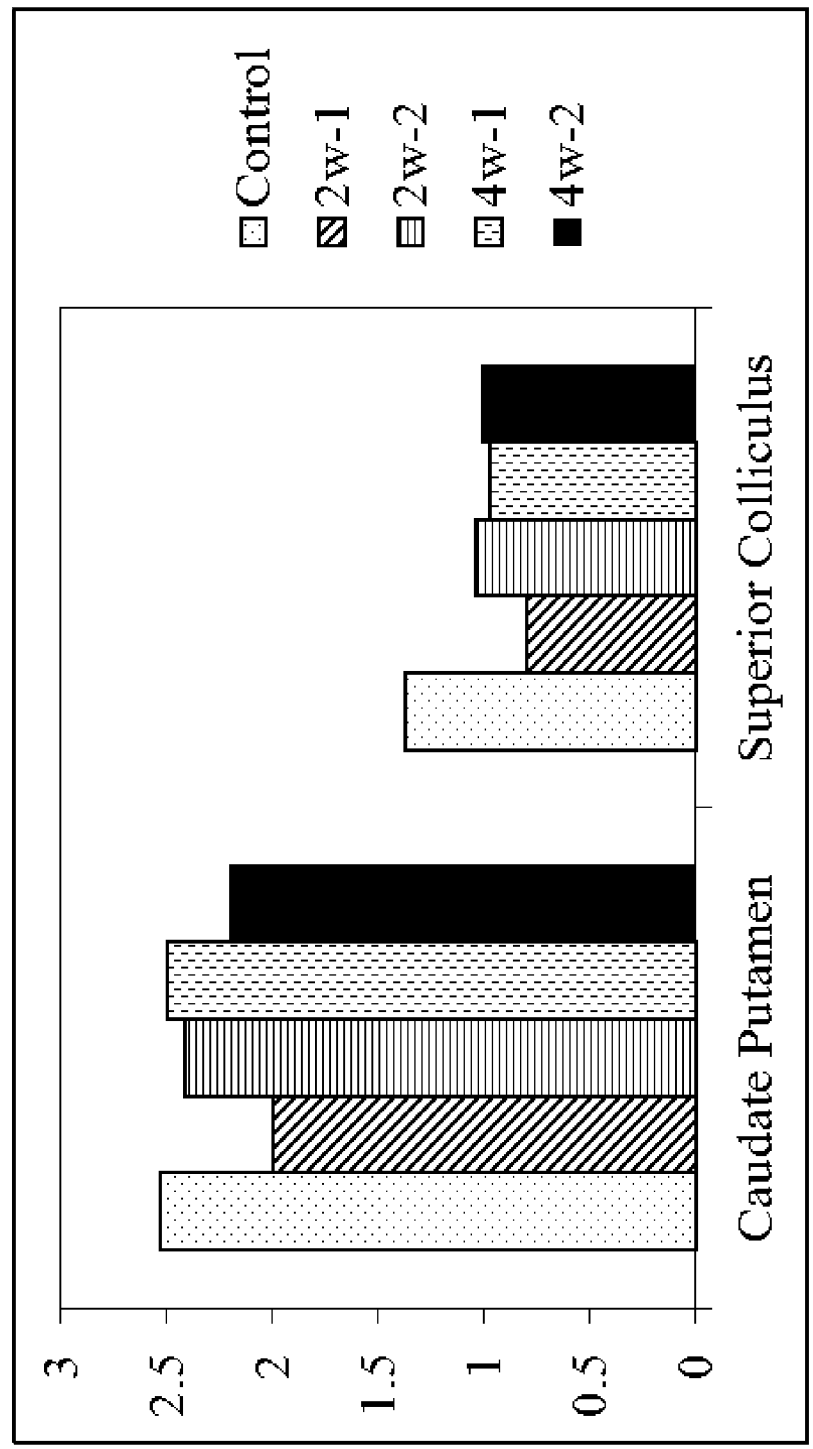

METHOD FOR INDUCING DOPAMINE PRODUCTION OF DOPAMINERGIC CELLS

BACKGROUND OF THE INVENTION

1. Field of the Invention

The present invention relates to a method for inducing a proliferation of dopaminergic cells and, more particularly, to a method for inducing a proliferation of dopaminergic cells with an herbal medicinal composition.

2. Description of Related Art

Parkinson's disease (PD) is a degenerative disorder of the central nervous system, resulting in a progressive movement disorder. It happens when the death of dopaminergic cells occur in the brain, and usually occurs after the age of 50. As the disease progresses, some movement-related symptoms including shaking, rigidity, slowness of movement and difficulty with walking and gait gradually occur, which may interrupt daily activities. In some worst cases, the patients may suffer from thinking and behavioral problems, and even depression.

Modern treatment for Parkinson's disease is the use of levodopa. Although many new drugs have been developed, including the dopamine agonists, levodopa is still considered the most effective drug for relieving the Parkinson's disease symptoms. However, as the disease progresses and more and more dopaminergic cell death occurs, levodopa eventually becomes ineffective.

Hence, it is desirable to provide a method for inducing a proliferation of dopaminergic cells, which may solve the problem of the dopaminergic cell death in brain, to effectively treat Parkinson's disease.

SUMMARY OF THE INVENTION

The object of the present invention is to provide an herbal medicinal composition and a method for inducing a proliferation of dopaminergic cells (also called as dopaminergic neurons, and dopamine-generating cells) in a subject in need using the same to increase dopamine secretion in the subject.

In addition, another object of the present invention is to provide an herbal medicinal composition and a method for treating Parkinson's disease using the same.

The herbal medicinal composition of the present invention comprises: *Ginseng* Radix, *Glycyrrhiza uralensis*, *Zingiber officinale* Roscoe, *Cinnamomum cassia* Presl., and Scutellariae Radix.

The method for inducing a proliferation of dopaminergic cells in a subject in need of the present invention comprises: administering the aforementioned herbal medicinal composition to a subject in need.

In addition, the method for treating Parkinson's disease of the present invention comprises: administering the aforementioned herbal medicinal composition to a subject in need.

The herbal medicinal composition of the present invention mainly comprises: *Ginseng* Radix, *Glycyrrhiza uralensis, Zingiber officinale* Roscoe, *Cinnamomum cassia* Presl., and Scutellariae Radix. Preferably, the herbal medicinal composition comprises: 1.0-5.0 parts by weight of the *Ginseng* Radix, 1.0-5.0 parts by weight of the *Glycyrrhiza uralensis*, 1.0-5.0 parts by weight of the *Zingiber officinale* Roscoe, 1.0-5.0 parts by weight of the *Cinnamomum cassia* Presl., and 0.1-3.0 parts by weight of the Scutellariae Radix. More preferably, the *Ginseng* Radix is comprised in an amount of 2.0-4.0 parts by weight, the *Glycyrrhiza uralensis* is comprised in an amount of 2.0-4.0 parts by weight, the *Zingiber officinale* Roscoe is comprised in an amount of 2.0-4.0 parts by weight, the *Cinnamomum cassia* Presl. is comprised in an amount of 2.0-4.0 parts by weight, and the Scutellariae Radix is comprised in an amount of 0.5-1.5 parts by weight. Further preferably, the *Ginseng* Radix is comprised in an amount of 2.8-3.2 parts by weight, the *Glycyrrhiza uralensis* is comprised in an amount of 2.8-3.2 parts by weight, the *Zingiber officinale* Roscoe is comprised in an amount of 2.8-3.2 parts by weight, the *Cinnamomum cassia* Presl. is comprised in an amount of 2.8-3.2 parts by weight, and the Scutellariae Radix is comprised in an amount of 0.8-1.2 parts by weight. Most preferably, the *Ginseng* Radix is comprised in an amount of approximately 3.0 parts by weight, the *Glycyrrhiza uralensis* is comprised in an amount of approximately 3.0 parts by weight, the *Zingiber officinale* Roscoe is comprised in an amount of approximately 3.0 parts by weight, the *Cinnamomum cassia* Presl. is comprised in an amount of approximately 3.0 parts by weight, and the Scutellariae Radix is comprised in an amount of approximately 1.0 parts by weight.

In the present invention, the *Ginseng* Radix may be also called as *Panax ginseng*, or *Ginseng* root; the *Glycyrrhiza uralensis* may be also called as Glycyrrhizae Radix, Liquorice, Licorice, or *glycyrrhiza*; the *Zingiber officinale* Roscoe may be also called as dried ginger, or Zingiberis Rhizoma; the *Cinnamomum cassia* Presl. may be also called as *Cinnamomum cassia*; and the Scutellariae Radix may be also called as *Scutellaria baicalensis*.

According to the requirement for use, the herbal medicinal composition of the present invention may further comprise at least one of a pharmaceutically acceptable carrier, a diluent, or an excipient generally used in the art. For example, the herbal medicinal composition is encapsulated into liposome to facilitate delivery and absorption; the herbal medicinal composition is diluted with aqueous suspension, dispersion or solution to facilitate injection; or the herbal medicinal composition is prepared in a form of a capsule or tablet for storage and carrying. In addition, the herbal medicinal composition of the present invention may also be administered with any conventional drug or additive together, as long as the treatment effect of the herbal medicinal composition of the present invention are not decreased.

The formulation of Chinese medicine composition emphasizes the principle of "Jun-Chen-Zuo-Shi"; in which "Jun" (emperor) refers to the component for treating the main cause of the disease, "Chen" (minister) refers to the component for enhancing the actions of "Jun" or treating accompanying symptoms "Zuo" (adjuvant) refers to the component for reducing or eliminating possible toxic effects of the Jun or Chen herbs but also treating accompanying symptoms, and "Shi" (courier) refers to the component for facilitating the delivery or guide of the other herbs to the target organs. Briefly, Chinese medicine composition is a prescription, which can combine the properties between drugs to comply with each other.

In addition, the herbal medicinal composition of the present invention can be prepared by any method known in the art, such as an extraction process using water or alcohols. Preferably, the herbal medicinal compositions prepared by a method comprising the following steps: mixing the *Ginseng* Radix, the *Glycyrrhiza uralensis*, the *Zingiber officinale*

Roscoe, the *Cinnamomum cassia* Presl., and the Scutellariae Radix to form a mixture; and extracting the mixture with water under heating.

In the present invention, during the step for extracting the mixture, the temperature and the time therefor are not particularly limited. Preferably, the mixture is extracted at a temperature of 90-100° C. for 60-90 minutes. In addition, the amount of the used water is also not particularly limited. Preferably, the water is used in an amount of 5-15 times the weight of the herbal medicinal composition. Furthermore, the step for extracting the mixture is preferably finished when a final volume of the mixture and the water is a half to a quarter of a beginning volume of the mixture and the water before the step for extracting the mixture.

When the subject in need is administered with the herbal medicinal composition of the present invention, dopaminergic cells in the subject can be proliferated, and therefore the dopamine secretion therein can further be increased. It is known that the motor symptoms of Parkinson's disease result from the death of dopaminergic cells (also called as dopamine-generating cells). Hence, by administering the herbal medicinal composition of the present invention, it is possible to treat Parkinson's disease due to the proliferation of the dopaminergic cells. Especially, the herbal medicinal composition of the present invention can induce the proliferation of the dopaminergic cells and therefore, it is possible to be used to prevent Parkinson's disease.

In the present invention, the term "treating" used in the present invention refers to the application or administration of the herbal medicinal composition to a subject with Parkinson's disease, in order to alleviate, relieve, alter, remedy, ameliorate, improve, or affect the disease. Also, the term "dopaminergic cells" used herein refers to the cells capable of secreting dopamine.

Other objects, advantages, and novel features of the invention will become more apparent from the following detailed description when taken in conjunction with the accompanying drawings.

BRIEF DESCRIPTION OF THE DRAWINGS

FIG. 1 is a diagram showing specific binding ratios of [$^{123}$I]Epidepride in mice after treating with the herbal medicinal composition of the present invention.

DETAILED DESCRIPTION OF THE PREFERRED EMBODIMENT

According to the specific embodiments illustrating the practice of the present invention, a person having ordinary skill in the art can easily understand other advantages and efficiency of the present invention through the content disclosed therein. The present invention can also be practiced or applied by other variant embodiments. Many other possible modifications and variations of any detail in the present specification based on different outlooks and applications can be made without departing from the spirit of the invention.

Preparation of Herbal Medicinal Composition

Ginseng Radix (11.25 g), *Glycyrrhiza uralensis* (11.25 g), *Zingiber officinale* Roscoe (11.25 g), *Cinnamomum cassia* Presl. (11.25 g), and Scutellariae Radix (3.75 g) were cut into slices if necessary, and then heated with water (3500 g) at 90° C. or more for 60 to 90 minutes to form an extract (540 g) divided into three equal parts. Herbal residues were removed from the extract after the extracting process. These herbal medicinal materials were selected and decocted under Dr Lee's (Yu Sheng Clinic) supervision. In addition, the aforementioned herbal medicinal composition was extracted by automatic medicinal herb decocting device (AMOS DP-200). Furthermore, most of herbal medicinal materials were produced from Mainland China and imported into Taiwan, and only a part of medicinal materials were locally produced in Taiwan.

Preparation of [$^{123}$I]Epidepride

[$^{123}$I]Epidepride was prepared by the same method disclosed in US 2012/0264949. Briefly, a precursor of Sn-Epidepride (150~250 μg) was added into methanol (50~150 μl). After being oscillated, a mixed solution of Sn-Epidepride was obtained. Next, the mixed solution of Sn-Epidepride was mixed with a solution of [$^{123}$I]ammonium iodide (NH$_4$I) (200~300μl), and followed by mixing with a solution of hydrogen peroxide (50~150 μl) to process destannylation. Then, the obtained was mixed with a solution of 39% sodium bisulfite (250~350 μl) to stop destannylation, and a saturated buffer solution of disodium hydrogen phosphate (1~3 ml) was added therein to neutralize the crude product. The crude product was introduced into a C18 column for washing out un-reacted I-123 ions by sterile water, and then the C18 column was eluted with 100% dehydrated alcohol (450~550 μl) to obtain purified [$^{123}$I]Epidepride.

Administration of Herbal Medicinal Composition

One dose (50 μl/dose) or double doses (100 μl/dose) of the aforementioned prepared herbal medicinal composition was orally administered to mice to be detected by [$^{123}$I]Epidepride SPECT imaging for 2 weeks or 4 weeks. In addition, one mouse without taking the aforementioned prepared herbal medicinal composition was classified as a control.

Experiment animals were injected with the prepared [$^{123}$I]Epidepride (5 mCi) about 185 MBq via the tail vein. After 30 minutes distribution, used isofurane gas (1 ml per minute) to anesthetize animals which were then placed inside on the nanoSPECT/CT (BioScan NanoSPECT/CT Plus). Then, the tomography image used the pin-holes to draw on the image for 30 minutes.

After the nanoSPECT image was completed, nanoCT Image was taken on the same place of the animal Software (FUJIFILM Multi Gauge) was used to mask the region, to reduce the background value of interest. Selected series brain region (compared with CT) and a non-brain region as image analysis of location (reference). Irregular regions of interest (ROIs) were drawn with the help of a brain atlas in areas corresponding to the left and right caudate putamen and superior colliculus, and the cerebellum was assumed to represent nonspecific bound and free radioactivity and used as a reference region. The specific binding ratios (SBRs) of [$^{123}$I]Epidepride in caudate putamen and superior colliculus were calculated by the following equation I.

$$\text{Specific binding ratio} = \frac{(\text{brain region} - \text{cerebellum})}{\text{cerebellum}} \quad \text{Equation I}$$

The obtained results are shown in FIG. 1 and the following Table 1, wherein the Y-axis in FIG. 1 is the SBR values.

TABLE 1

| SBR | Control | 2w-1 | 2w-2 | 4w-1 | 4w-2 |
|---|---|---|---|---|---|
| Caudate Putamen | 2.53 | 2.00 | 2.42 | 2.50 | 2.20 |

TABLE 1-continued

| SBR | Control | 2w-1 | 2w-2 | 4w-1 | 4w-2 |
|---|---|---|---|---|---|
| Superior Colliculus | 1.38 | 0.80 | 1.04 | 0.98 | 1.01 |

"2w-1" refers to the mouse administered one dose for 2 weeks.
"2w-2" refers to the mouse administered double doses for 2 weeks.
"4w-1" refers to the mouse administered one dose for 4 weeks.
"4w-2" refers to the mouse administered double doses for 4 weeks.

[$^{123}$I]Epidepride is an imaging agent for identifying dopamine $D_2$ receptors, and competitive with dopamine to bind dopamine $D_2$ receptors. Hence, as the dopamine secretion increased, the SBR values decreased. According to the results shown in FIG. 1 and Table 1, it can be found that the SBR values were decreased when the herbal medicinal composition was administered into the mice, indicating that dopaminergic cells were proliferated to secrete more dopamine after herbal medicinal composition administration. Hence, the herbal medicinal composition of the present invention can induce the proliferation of dopaminergic cells and, therefore, be used for treating Parkinson's disease.

Although the present invention has been explained in relation to its preferred embodiment, it is to be understood that many other possible modifications and variations can be made without departing from the spirit and scope of the invention as hereinafter claimed.

What is claimed is:

1. A method for inducing increased dopamine secretion by dopaminergic cells in a subject having Parkinson's disease, comprising:
  (i) providing an herbal medicinal composition, wherein the herbal medicinal composition comprises therapeutically effective amounts of extracts of each of *Ginseng* Radix, *Glycyrrhiza* Radix, *Zingiber* Rhizoma, *Cinnamomum cassia* Presl., and Scutellariae Radix; and wherein the herbal medicinal composition comprises by weight thereof:
    (a) 1.0 to 5.0 parts by weight of the *Ginseng* Radix extract,
    (b) 1.0 to 5.0 parts by weight of the *Glycyrrhiza* Radix extract,
    (c) 1.0 to 5.0 parts by weight of the *Zingiber* Rhizoma extract,
    (d) 1.0 to 5.0 parts by weight of the *Cinnamomum cassia* Presl. extract, and
    (e) 0.1 to 3.0 parts by weight of the Scutellariae Radix extract; and
  (ii) orally administering the herbal medicinal composition to a subject having Parkinson's disease, in a dosing amount thereof sufficient to induce increased dopamine secretion by dopaminergic cells in the subject.

2. The method as claimed in claim 1, wherein the herbal medicinal composition comprises by weight thereof:
  the *Ginseng* Radix extract in an amount of 2.0 to 4.0 parts by weight;
  the *Glycyrrhiza* Radix extract in an amount of 2.0 to 4.0 parts by weight;
  the *Zingiber* Rhizoma extract in an amount of 2.0 to 4.0 parts by weight;
  the *Cinnamomum cassia* Presl. extract in an amount of 2.0 to 4.0 parts by weight; and
  the Scutellariae Radix extract in an amount of 0.5 to 1.5 parts by weight.

3. The method as claimed in claim 2, wherein the herbal medicinal composition comprises by weight thereof:
  the *Ginseng* Radix extract in an amount of 2.8 to 3.2 parts by weight;
  the *Glycyrrhiza* Radix extract in an amount of 2.8 to 3.2 parts by weight;
  the *Zingiber* Rhizoma extract in an amount of 2.8 to 3.2 parts by weight;
  the *Cinnamomum cassia* Presl. extract in an amount of 2.8 to 3.2 parts by weight; and
  the Scutellariae Radix is comprised in an amount of 0.8 to 1.2 parts by weight.

4. The method as claimed in claim 1, wherein the herbal medicinal composition further comprises one or more member selected from the group consisting of a pharmaceutically acceptable carrier, a diluent, and an excipient.

5. The method as claimed in claim 1, wherein the herbal medicinal composition is a composition prepared by a process comprising:
  mixing amounts of *Ginseng* Radix, *Glycyrrhiza* Radix, *Zingiber* Rhizoma, *Cinnamomum cassia* Presl., and Scutellariae Radix to form an herbal mixture, wherein the *Glycyrrhiza* Radix is *Glycyrrhiza uralensis* Radix and the *Zingiber* Rhizoma is *Zingiber officinale* Roscoe Rhizoma;
  extracting the herbal mixture by contacting with water under heating for a period of time sufficient to obtain an aqueous extract, and
  purifying the aqueous extract by removing herbal residues therefrom, thereby obtaining the herbal medicinal composition.

6. The method as claimed in claim 5, wherein the heating temperature is a temperature of 90° C. to 100° C. and the period of time is from 60 minutes to 90 minutes.

7. The method as claimed in claim 5, wherein the water is used in an amount of 5-15 times the weight of the herbal medicinal composition.

8. A method for treating Parkinson's disease in a subject suffering therefrom, comprising:
  providing an herbal medicinal composition, wherein the herbal medicinal composition comprises therapeutically effective amounts of extracts of each of *Ginseng* Radix, *Glycyrrhiza* Radix, *Zingiber* Rhizoma, *Cinnamomum cassia* Presl., and Scutellariae Radix; and wherein the herbal medicinal composition comprises by weight thereof:
    (a) 1.0 to 5.0 parts by weight of the *Ginseng* Radix extract,
    (b) 1.0 to 5.0 parts by weight of the *Glycyrrhiza uralensis* Radix extract,
    (c) 1.0 to 5.0 parts by weight of the *Zingiber officinale* Rhizoma extract,
    (d) 1.0 to 5.0 parts by weight of the *Cinnamomum cassia* Presl. extract, and
    (e) 0.1 to 3.0 parts by weight of the Scutellariae Radix extract; and
  orally administering the herbal medicinal composition to a subject having Parkinson's disease, in a dosing amount thereof sufficient to induce increased dopamine secretion by dopaminergic cells in the subject, thereby treating said Parkinson's disease in the subject.

* * * * *